Figure 1:
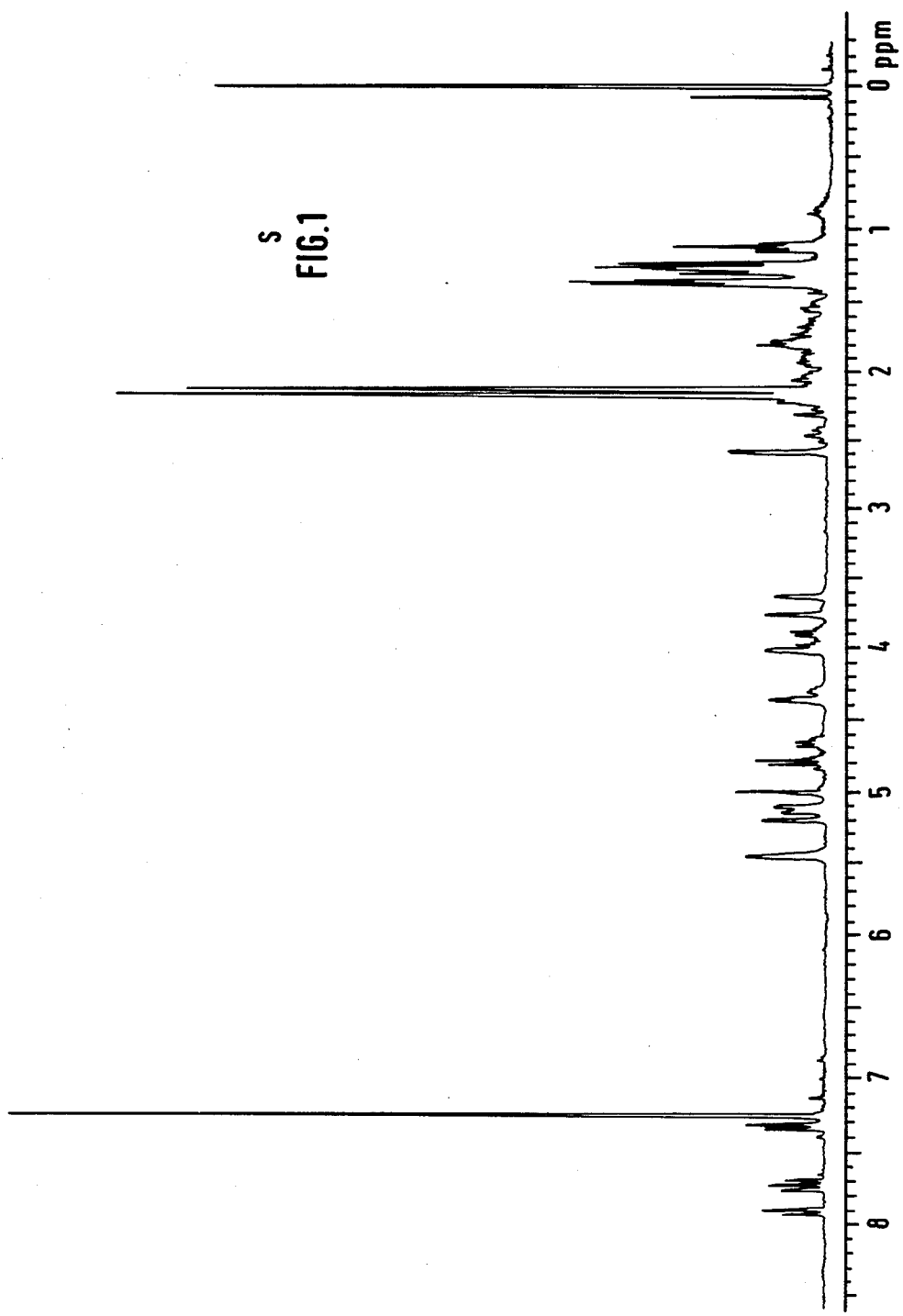

United States Patent [19]

Huber et al.

[11] Patent Number: 4,737,583
[45] Date of Patent: Apr. 12, 1988

[54] ANTHRACYCLIN DERIVATIVES

[75] Inventors: Gerhard Huber, Kelkheim; Hans G. Berscheid, Schwalbach; Hans-Wolfram Fehlhaber, Marburg, all of Fed. Rep. of Germany

[73] Assignee: Hoechst Aktiengesellschaft, Fed. Rep. of Germany

[21] Appl. No.: 47,491

[22] Filed: May 5, 1987

Related U.S. Application Data

[63] Continuation of Ser. No. 631,724, Jul. 17, 1984, abandoned.

[30] Foreign Application Priority Data

Jul. 19, 1983 [DE] Fed. Rep. of Germany ....... 3325957

[51] Int. Cl.$^4$ ............................................. C07H 15/24
[52] U.S. Cl. ...................................................... 536/6.4
[58] Field of Search .......................... 536/6.4; 514/34

[56] References Cited

U.S. PATENT DOCUMENTS 4,316,011  2/1982  Oki et al. .............................. 536/6.4

OTHER PUBLICATIONS

J. Antibiotics, vol. 36(5):83–65 (May 1983).
J. Antibiotics, vol. 29(12):76–116 (Dec. 1976).
J. Antibiotics, vol. 36(8):1080–1083 (Aug. 1983).
EP-A2-131 181 to Aretz et al (Hoechst A.G.).
EP-A1-0 110 115 to Umezawa et al. (Microbiology Chemistry Research Foundation).
Certified Translation of German Priority Document P 33 25 957.7.

*Primary Examiner*—J. R. Brown
*Assistant Examiner*—Elli Peselev
*Attorney, Agent, or Firm*—Finnegan, Henderson, Farabow, Garrett & Dunner

[57] ABSTRACT

The present invention relates to anthracyclin derivatives of the formula I

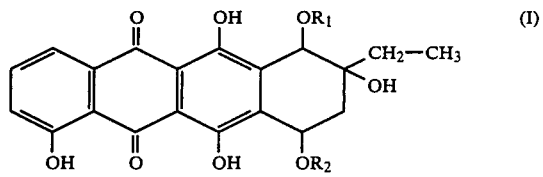

in which $R_1$ and $R_2$ are identical or different and represent the sugar residue Roa (L—rhodosamine) of the formula

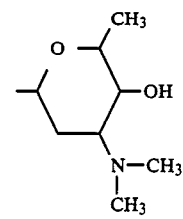

or the sugar combination Roa—dF=CinB (dF=2-deoxy-L-fucose; CinB=L-cinerulose B) of the formula

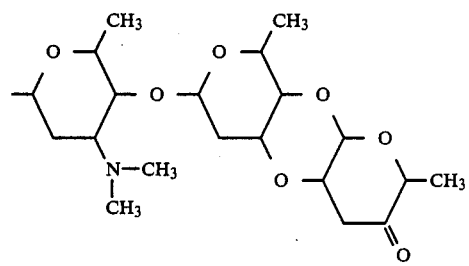

The invention furthermore relates to a process for the preparation of the above compounds of the formula I, and to their use as cytostatic agents.

3 Claims, 2 Drawing Sheets

ANTHRACYCLIN DERIVATIVES

This application is a continuation, of application Ser. No. 631,724, filed July 17, 1984, now abandoned.

The present invention relates to anthracyclin derivatives of the formula I

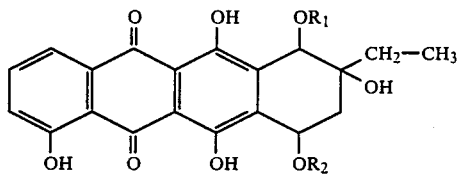

in which $R_1$ and $R_2$ are identical or different and represent the sugar residue Roa (L—rhodosamine) of the formula

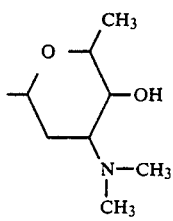

or the sugar combination Roa—dF=CinB (dF=2-deoxy-L-fucose; CinB=L-cinerulose B) of the formula

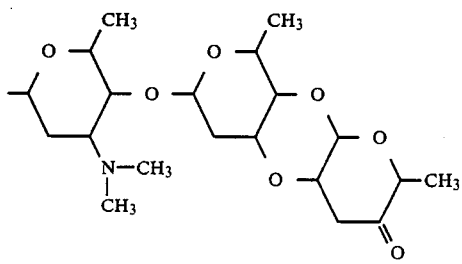

The invention furthermore relates to a process for the preparation of the above compounds of the formula I, which comprises treating, with a weak acid, the residue prepared according to German Patent Application No. P 33 23 025.0(corresponding to U.S Application Ser. No. 824,374 by fermentation of the microorganism strain Y-11472 deposited on 24.5.1983 under serial number DSM 2658 at the "Deutsche Sammlung von Mikroorganismen" ("German Collection of Microorganisms")) and extraction of the mycelium and the culture filtrate with an organic solvent.

The compounds thus prepared are distinguished by a powerful cytostatic activity.

According to the abovementioned German patent application, the strain Streptomyces Y-11472 is fermented in a nutrient medium in the customary manner, temperatures of about 24°–40° C., a pH of 6.5–8.5 and aerobic conditions being maintained. The anthracyclin compounds are extracted from the mycelium by extraction, for example with aqueous acetone at a pH of 3.5, the acetone is removed and the aqueous phase is extracted at a pH of 7.5 with ethyl acetate. The culture liquid is extracted at a pH of 7.5, preferably with ethyl acetate. The ethyl acetate extracts from the mycelium and the culture filtrate are combined and, when evaporated to dryness, give a crude residue. The residue thus obtained can now be subjected to an acid treatment according to the invention. However, the residue is preferably further worked up, as also described in the above German patent application.

The crude residue is accordingly dissolved in toluene and the solution is extracted with an acetate buffer (ph 3.5) a toluene phase and an aqueous phase being obtained. The aqueous phase is further worked up in the following manner: after the pH has been adjusted to 7.5, the aqueous phase is again extracted with ethyl acetate and the ethyl acetate phase is concentrated, a so-called crude cytorhodin mixture being obtained. According to the above German patent application, anthracyclin derivatives with a cytostatic activity can be obtained from this crude mixture by a chromatographic route.

It has now been found, surprisingly, that novel anthracyclins having also cytostatic activity are obtained if the crude residue described above or the so-called crude cytorhodin mixture is treated with a dilute strong or moderately strong acid. Examples of suitable acids are dilute hydrochloric acid, sulfuric acid, phosphoric acid, formic acid, acetic acid and trifluoroacetic acid, and other acids, if appropriate also after addition of a water-miscible organic solvent, for example methanol or acetone. The acid treatment can also be carried out with strongly acid ion exchangers in the H form, such as, for example, Dowex 50×8 [H+]. In this case, the desired product must be obtained by elution from the ion exchanger, for example with salt solutions.

The acid treatment is carried out at room temperature or slightly elevated temperature, preferably 37° C. The reaction time can be 0.5 to several hours. After the acid has been bound, the desired compounds are isolated from the reaction medium by extraction and separated by column chromatography, preferably on silica gel.

The following compounds, for example, are obtained by the process according to the invention:

Cytorhodin S

Red, amorphous substance, readily soluble in methanol, ethyl acetate, chloroform and toluene, insoluble in water and hexane.

Thin Layer chromatography: silica gel 60F$_{254}$ "Merck"

System B: chloroform/methanol/glacial acetic acid/water 70:20:10:2, RF=0.67

UV maxima: 236, 252 (shoulder), 293, 497 and 563 nm in methanol/10% 1N HCl

NMR spectrum: FIG. 1 $C_{48}H_{64}N_2O_{17}$, M Calc. 940 (FAB-MS confirmed

Cytorhodin S has the formula I, in which $R_1$ denotes —Roa and $R_2$ denotes —Roa—dF=CinB.

Cytorhodin T

Red, amorphous substance, readily soluble in methanol, ethyl acetate, chloroform and toluene, insoluble in water and hexane.

Thin layer chromatography: silica gel 60F$_{254}$ "Merck"

System B: chloroform/methanol/glacial acetic acid/water 70:20:10:2, RF=0.53

UV maxima: 236, 252 (shoulder), 293, 496 and 563 nm in methanol/10% 1N HCl

Figure 2:
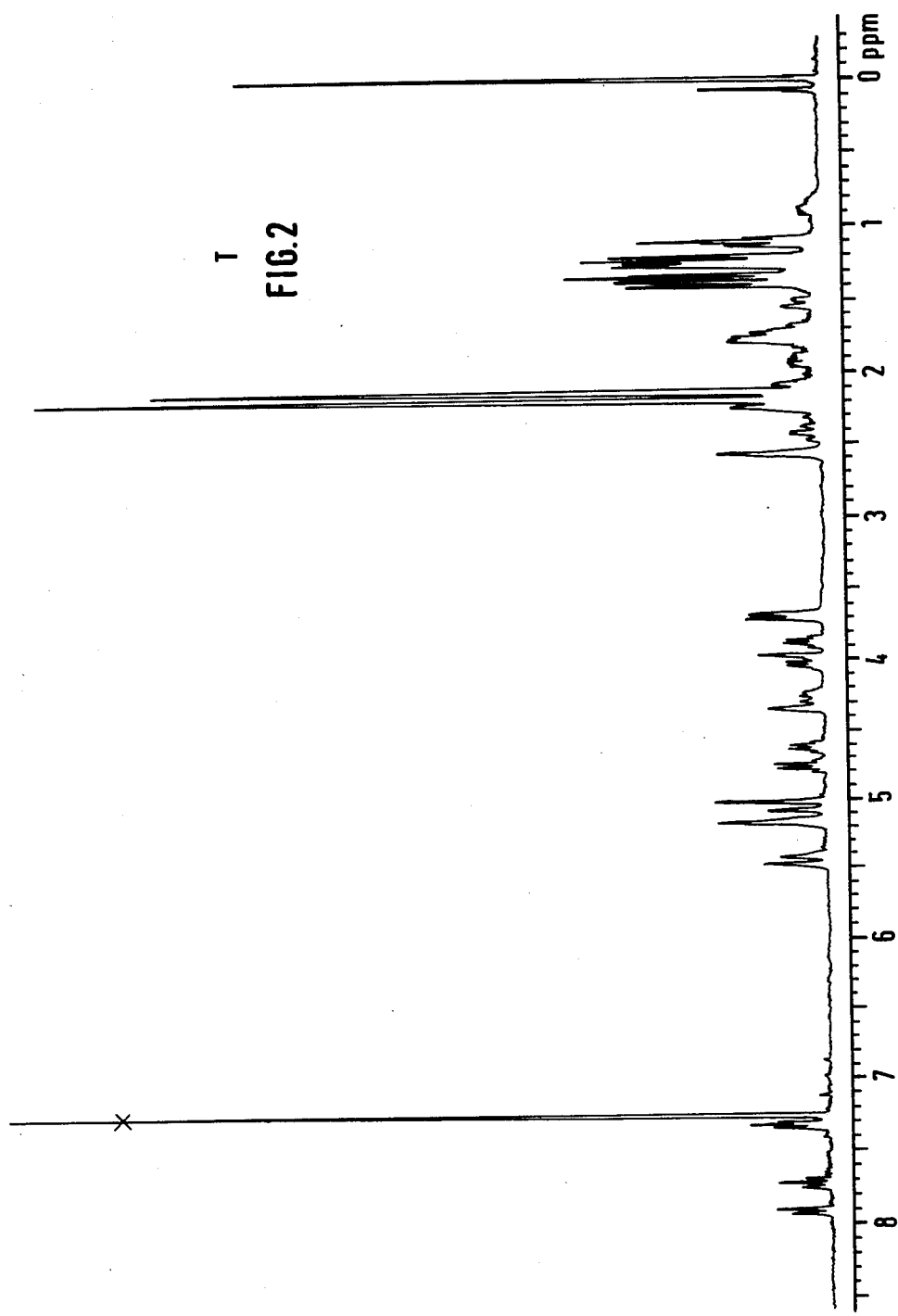

NMR spectrum: FIG. 2 $C_{48}H_{64}N_2O_{17}$, M Calc. 940 (FAB-MS Confirmed)

Cytorhodin T has the formula I in which $R_1$ denotes —Roa—dF=CinB and $R_2$ denotes —Roa.

Besides the novel cytorhodins, β-rhodomycin II, which is already known (Rhodomycin A, H. Brockmann et al., Naturwiss. 37, 492, 1950; ibid 42, 154, 1955) is also formed (formula I, in which $R_1$ and $R_2$ each denote —Roa).

The cytorhodins according to the invention are distinguished by a powerful cytostatic activity and gave the following action on L1210 leukemia cells in the cell proliferation test:

|  | $IC_{50}$ (μg/ml) |
|---|---|
| Cytorhodin S | $3 \times 10^{-4}$ |
| Cytorhodin T | $2 \times 10^{-3}$ |

The inhibiting action is determined as follows (cell proliferation test):

L1210 cells in the exponential growth phase ($5 \times 10^3$/ml in RPMI 1640) are incubated with various concentrations of the test substance in a microtiter plate for 72 hours (37° C., 5% of $CO_2$, 95% relative atmospheric humidity). Controls comprise cells which are incubated only with fresh medium. All the determinations are carried out as quadruplicate determinations. After 65 hours, 50 μl of C14-thymidine (1.5 μC/ml) are added in order to radioactively label the DNA of the cells. After incubation for 7 hours, the cells are filtered off with suction and the DNA is precipitated with 5% strength trichloroacetic acid and washed successively with water and methanol. After drying at 50° C., the radioactivity incorporated into the DNA is determined, after addition of 5 ml of scintillation liquid. The results are given as the relationships of the scintillation index after incubation with test substance in percent of the untreated control. From the measurement values thus obtained, the dose effect curve is established and the $IC_{50}$, i.e. the concentration which, under test conditions, reduces the incorporation of radioactive thymidine by 50% compared with the control, is determined graphically.

The preparation of the compounds according to the invention is described in the following examples:

EXAMPLE 1

4.5 g of crude cytorhodin complex are dissolved in 250 ml of 0.2N HCl and the solution is warmed at 37° C. for 1 hour. It is brought to pH 7.5 with cooled 1N NaOH and extracted 4 times with 300 ml of chloroform each time. The chloroform extract is evaporated to dryness in vacuo. The residue (2.1 g) is dissolved in 30 ml of a mixture of chloroform/methanol/glacial acetic acid/water 50:50:5:2 (system A) and applied to a column of 200 ml of silica gel 60 "Merck", 40–63μ, suspended in system A, and is eluted with the same system A. After a forerun of 100 ml, 10 ml fractions are collected and are analyzed by thin layer chromatography (silica gel 60F$_{254}$ "Merck", system B: chloroform/methanol/glacial acetic acid/water 70:20:10:2). The active substances appear in the following fractions:
18–31: cytorhodin S and T
45–67: β-rhodomycin II Fractions 18–31 are combined, 5% strength aqueous $Na_2HPO_4$ solution is added until the chloroform phase separates out, the chloroform phase is washed with 1 volume each of $Na_2HPO_4$ solution and water, dried over anhydrous sodium sulfate and concentrated in vacuo and the residue is precipitated with hexane.

Yield: 540 mg of a mixture of the components cytorhodin S and T.

EXAMPLE 2

300 mg of the mixture of cytorhodin S and T obtained according to Example 1 are dissolved in 20 ml of system B (see Example 1) and the solution is applied to a column of 100 ml of silica gel 60 "Merck", 15–40μ, suspended in the same system, and is eluted with system B. After a forerun of 100 ml, active fractions of 5 ml each are collected:

| 21–32 | cytorhodin S | 160 mg |
|---|---|---|
| 41–80 | cytorhodin S + a little T | 35 mg |
| 81–100 | cytorhodin T | 40 mg |

5% strength aqueous $Na_2HPO_4$ solution is added to the combined fractions until the chloroform phase separates out, this phase is washed with 1 volume each of $Na_2HPO_4$ solution and water, dried over anhydrous sodium sulfate and concentrated in vacuo and the residue is precipitated with hexane.

Yield:
160 mg of pure cytorhodin S.
40 mg of pure cytorhodin T

EXAMPLE 3

1.1 g of cytorhodin complex are dissolved in 60 ml of 0.2N formic acid and the solution is warmed at 37° C. for 24 hours. The solution, which, according to thin layer chromatography, contains cytorhodins S and T, is brought to pH 7.5 with 1N NaOH and worked up as in Example 1.

EXAMPLE 4

0.64 ml of trifluoroacetic acid is added to a solution of 0.5 g of cytorhodin complex in 28 ml of $H_2O$, with stirring, and the mixture is then left to stand at room temperature for 4 hours. The solution is worked up to give cytorhodins S and T as in Examples 1 and 2.

The components in the preceding examples were identified using the conditions of measurement described below:

The proton resonance spectra ($^1$H-NMR spectra) were recorded at 270 MHz using an HX-270 BRUKER Fourier transform nuclear magnetic resonance spectrometer. The concentrations were 2–4 mg/0.5 ml of 99.8% CDCl$_3$; immediately after preparation, the solutions were shaken with 0.1 ml of 5% $Na_2CO_3$ in 99.5% $D_2O$.

The signals identified by an asterisk in the figures derive from low molecular weight contamination, in the $10^{-3}$ range, and from residual solvent.

The mass spectra were recorded using an MS-902 S, AEI, mass specgrometer using an FAB (fast atom bombardment) ion source. The substances were inserted in a matrix of thioglycerol into the ion source, ammonium chloride sometimes being added.

We claim:
1. A compound of the formula I

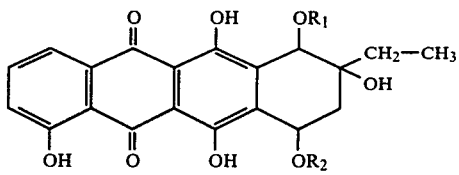

in which $R_1$ and $R_2$ are identical or different and can have the following meaning:

—Roa of the formula

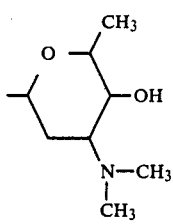

or —Roa—dF═CinB of the formula

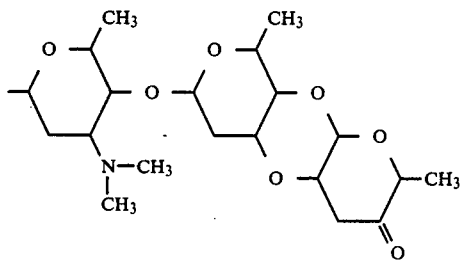

with the exception of the compound of the formula I in which $R_1$ and $R_2$ both denote Roa.

2. The compound of formula I as claimed in claim 1, in which $R_1$ denotes —Roa of the formula II

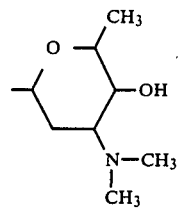

and $R_2$ denotes —Roa—dF═CinB

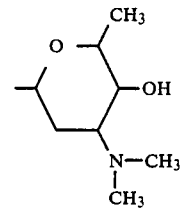

of the formula III.

3. The compound of formula I as claimed in claim 1, in which $R_1$ denotes —Roa—dF═CinB of the formula III

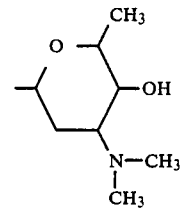

and $R_2$ denotes —Roa

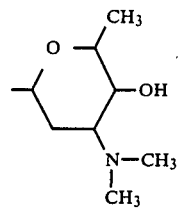

* * * * *

UNITED STATES PATENT AND TRADEMARK OFFICE
CERTIFICATE OF CORRECTION

PATENT NO. : 4,737,583
DATED : April 12, 1988
INVENTOR(S) : Gerhard Huber et al.

It is certified that error appears in the above-identified patent and that said Letters Patent is hereby corrected as shown below:

ON THE TITLE PAGE:

Add as inventor --Hans P. Kraemer, Marburg, Federal Republic of Germany--.

Signed and Sealed this

Eleventh Day of April, 1989

*Attest:*

DONALD J. QUIGG

*Attesting Officer*  *Commissioner of Patents and Trademarks*